United States Patent
Cooper et al.

(10) Patent No.: US 10,842,529 B2
(45) Date of Patent: Nov. 24, 2020

(54) ENTRY GUIDE FOR MULTIPLE INSTRUMENTS IN A SINGLE PORT SURGICAL SYSTEM

(71) Applicant: INTUITIVE SURGICAL OPERATIONS, INC., Sunnyvale, CA (US)

(72) Inventors: Thomas G. Cooper, Menlo Park, CA (US); Anthony K. McGrogan, San Jose, CA (US); Paul E. Lilagan, Sunnyvale, CA (US); Daniel H. Gomez, Los Gatos, CA (US); Giuseppe Maria Prisco, Calci Pisa (IT)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 381 days.

(21) Appl. No.: 15/866,158

(22) Filed: Jan. 9, 2018

(65) Prior Publication Data
US 2018/0153578 A1 Jun. 7, 2018

Related U.S. Application Data

(63) Continuation of application No. 12/705,439, filed on Feb. 12, 2010, now Pat. No. 9,877,744.

(51) Int. Cl.
*A61B 17/34* (2006.01)
*A61B 1/00* (2006.01)
(Continued)

(52) U.S. Cl.
CPC ...... *A61B 17/3421* (2013.01); *A61B 1/00064* (2013.01); *A61B 34/30* (2016.02);
(Continued)

(58) Field of Classification Search
CPC . A61B 1/00135; A61B 1/00154; A61B 1/015; A61B 1/018; A61B 2017/3445; A61B 2017/3449; A61B 2017/3466
(Continued)

(56) References Cited

U.S. PATENT DOCUMENTS 4,538,594 A * 9/1985 Boebel ............... A61B 1/31
600/102
4,616,631 A 10/1986 Takahashi
(Continued)

FOREIGN PATENT DOCUMENTS

EP 1712248 A2 10/2006
WO WO-2008070556 A1 6/2008

OTHER PUBLICATIONS

PCT/US11/22832 International Search Report and Written Opinion of the International Searching Authority, dated Apr. 11, 2011, 10 pages.
(Continued)

*Primary Examiner* — John P Leubecker
(74) *Attorney, Agent, or Firm* — Haynes and Boone, LLP (57) ABSTRACT

A surgical access port comprises a seal and an instrument guide, which comprises proximal and distal ends, a plurality of instrument guide channels, and an outside surface that fits closely to an inner wall surface of a cannula into which the instrument guide is inserted. The seal is positioned to seal between the instrument guide and the inner wall surface as the instrument guide rotates within the cannula. A first guide channel is configured to support a first surgical instrument at a first defined position within the cannula. A second guide channel is configured to support a second surgical instrument at a second defined position within the cannula. A first guide channel opening is defined along a length of the first guide channel to be open to the outside surface of the
(Continued)

instrument guide and place a portion of the first surgical instrument adjacent the inner wall surface.

21 Claims, 6 Drawing Sheets

(51) Int. Cl.
    *A61B 90/11*           (2016.01)
    *A61B 34/30*           (2016.01)
    *A61B 17/00*           (2006.01)

(52) U.S. Cl.
    CPC ........... *A61B 90/11* (2016.02); *A61B 1/00135* (2013.01); *A61B 1/00154* (2013.01); *A61B 17/3474* (2013.01); *A61B 2017/003* (2013.01); *A61B 2017/00278* (2013.01); *A61B 2017/00309* (2013.01); *A61B 2017/00323* (2013.01); *A61B 2017/00362* (2013.01); *A61B 2017/3445* (2013.01); *A61B 2017/3449* (2013.01); *A61B 2017/3466* (2013.01)

(58) Field of Classification Search
    USPC .................................................. 600/104, 114
    See application file for complete search history.

(56) References Cited

U.S. PATENT DOCUMENTS

| | | | |
|---|---|---|---|
| 4,846,791 A | | 7/1989 | Hattler et al. |
| 5,817,013 A | | 10/1998 | Ginn et al. |
| 5,846,181 A | | 12/1998 | Heckele et al. |
| 5,944,654 A | * | 8/1999 | Crawford ............... A61B 1/127 |
| | | | 600/128 |
| 6,424,885 B1 | | 7/2002 | Niemeyer et al. |
| 6,616,600 B2 | * | 9/2003 | Pauker ............... A61B 1/00071 |
| | | | 600/128 |
| 6,991,602 B2 | | 1/2006 | Nakazawa et al. |
| 7,150,713 B2 | * | 12/2006 | Shener ............... A61B 1/00071 |
| | | | 600/156 |
| 7,762,949 B2 | * | 7/2010 | Nakao ................ A61B 1/00073 |
| | | | 600/104 |
| 8,162,895 B2 | | 4/2012 | Sniffin |
| 8,932,208 B2 | * | 1/2015 | Kendale ............. A61B 17/3478 |
| | | | 600/176 |
| 2004/0267254 A1 | | 12/2004 | Manzo et al. |
| 2005/0004431 A1 | | 1/2005 | Kogasaka et al. |
| 2007/0083217 A1 | * | 4/2007 | Eversull ................ A61B 1/018 |
| | | | 606/114 |
| 2008/0065105 A1 | | 3/2008 | Larkin et al. |
| 2008/0065110 A1 | | 3/2008 | Duval et al. |
| 2008/0188869 A1 | * | 8/2008 | Weitzner ............. A61B 1/0014 |
| | | | 606/130 |
| 2008/0287963 A1 | | 11/2008 | Rogers et al. |
| 2011/0082365 A1 | * | 4/2011 | McGrogan ......... A61B 1/00154 |
| | | | 600/424 |
| 2011/0201883 A1 | | 8/2011 | Cooper et al. |
| 2016/0175006 A1 | * | 6/2016 | Dejima ............. A61B 1/00112 |
| | | | 600/114 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

ENTRY GUIDE FOR MULTIPLE INSTRUMENTS IN A SINGLE PORT SURGICAL SYSTEM

PRIORITY INFORMATION

This application is a continuation of U.S. patent application Ser. No. 12/705,439, now U.S. Pat. No. 9,877,744, filed on Feb. 12, 2010, which is incorporated by reference herein in its entirety.

BACKGROUND

This invention relates to surgical cannulas, and more particularly, to a surgical cannula for introducing multiple minimally invasive surgical instruments through a single opening in the body.

Minimally invasive surgery (MIS) (e.g., endoscopy, laparoscopy, thoracoscopy, cystoscopy, and the like) allows a patient to be operated upon through small incisions by using a camera and elongated surgical instruments introduced to an internal surgical site. The surgical site often comprises a body cavity, such as the patient's abdomen. The body cavity may optionally be distended using a clear fluid such as an insufflation gas. In traditional minimally invasive surgery, the surgeon manipulates the tissues by using hand-actuated end effectors of the elongated surgical instruments while viewing the surgical site on a video monitor.

One or more cannulas may be passed through small (generally 1 inch or less) incisions or a natural body orifice to provide entry ports for the minimally invasive (e.g., endoscopic, laparoscopic, and the like) surgical instruments, including a camera instrument (e.g., endoscope, laparoscope, and the like). A surgeon is able to perform surgery by manipulating the surgical instruments externally to the surgical site under the view provided by the camera instrument.

It is typical to provide several cannulas for a minimally invasive surgical procedure. Generally each cannula will provide access to the surgical site for a single surgical or camera instrument. For example, four cannulas may be provided with one cannula being used to introduce a camera instrument and the remaining three cannulas being used to introduce surgical instruments. While the small incisions necessary for placing a cannula are less traumatic than the incision necessary for open surgery, each incision still represents a trauma to the patient.

In an effort to reduce the trauma of minimally invasive surgery even further, techniques are being developed to allow minimally invasive surgery using only a single cannula. This may be accomplished by using a somewhat larger cannula that can accommodate all of the instruments required for the surgery. Minimally invasive surgery performed through a single cannula may be referred to as single port access (SPA) surgery. The single cannula may be introduced through a body orifice and be referred to as Natural Orifice Transdermal Endoscopic Surgery (NOTES). Single port surgery may also be referred to as bellybutton surgery when the navel (umbilicus) is used as the location for the single cannula.

If multiple surgical instruments and/or camera instruments are to be introduced to a surgical site through a single cannula, it can become difficult manage the instruments within the cannula. It is desirable to use as small a cannula as possible consistent with the size of the instruments to be passed through the cannula. This may make it difficult to introduce the additional instruments and to maintain the necessary mobility of the instruments.

These difficulties may be even greater for robotically controlled minimally invasive surgical procedures because of the robotic controllers on the instruments. The robotic controllers may limit the visibility and accessibility of the cannula. The robotic controllers may render the instruments less agile with regard to introduction into the cannula.

In view of the above, it would be desirable to provide an improved cannula for carrying out minimally invasive surgical procedures that facilitates the introduction of multiple surgical instruments and/or camera instruments to a surgical site through a single compact cannula.

SUMMARY

An access port for use in single port surgery includes a cannula to provide minimally invasive access to a surgical site and an instrument guide that fits closely within the cannula. The instrument guide includes guide channels that are open to the outside surface of the instrument guide. Each of the guide channels is configured to support a single surgical instrument at a defined position within the cannula. The guide channels may be smoothly enlarged at the end that receives surgical instruments. The access port may further include a seal that couples the instrument guide to the cannula such that the seal retains a pressurized insufflation fluid within the surgical site. The instrument guide may include one or more insufflation channels for introducing an insufflation fluid to the surgical site. The access port may include a flexible section. The surgical instruments may be controlled robotically by servo actuators.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION

In the following description, numerous specific details are set forth. However, it is understood that embodiments of the invention may be practiced without these specific details. In other instances, well-known devices, structures and techniques have not been shown in detail in order not to obscure the understanding of this description.

Figure 1:
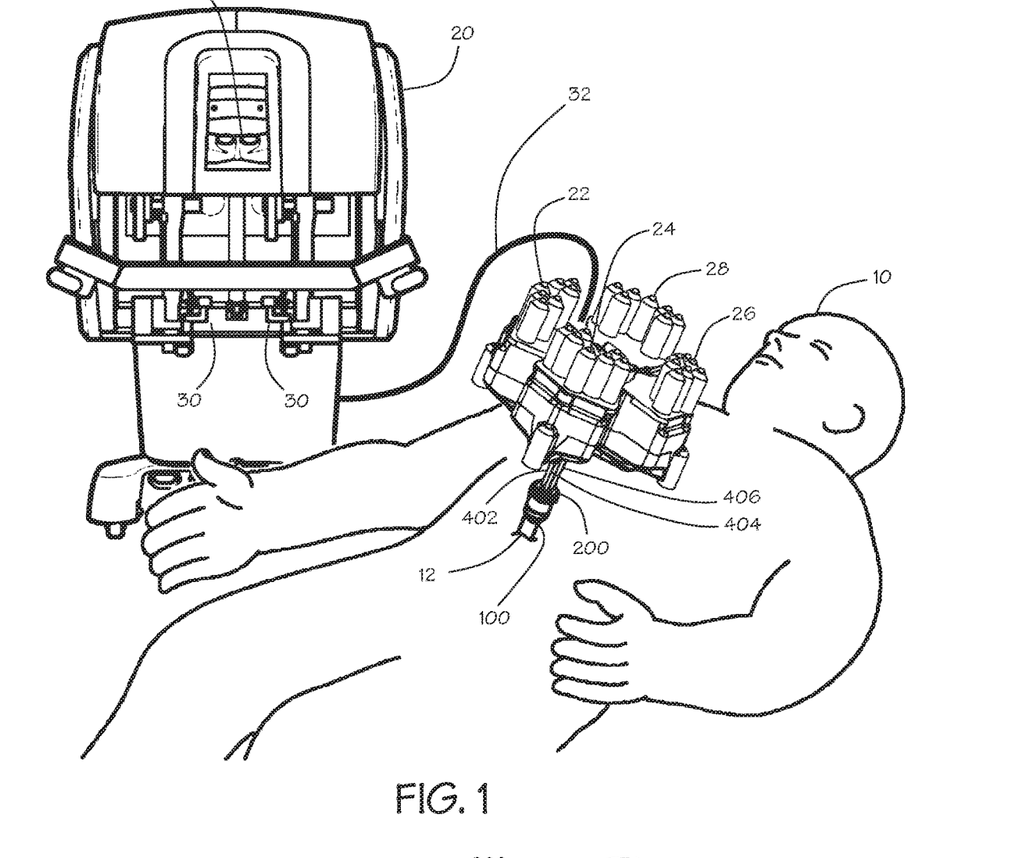
FIG. 1 is a perspective view of a master control workstation and a manipulator system for robotically moving a plurality of minimally invasive surgical instruments.

FIG. 1 shows a pictorial view of a minimally invasive surgery on a patient 10 using single port access 12 for robotic surgical instruments 402, 404, 406. Typically three or four surgical instruments, including a camera instrument, are introduced through the access port 12. In addition, there will generally be provisions for introducing an insufflation gas, such as carbon dioxide ($CO_2$), at or near the access port. It will be appreciated that single port surgery requires a substantial amount of equipment to be located in a small amount of space.

The robotic surgical instruments 402, 404, 406, which may include a camera instrument that may provide images of the surgical site and other instruments, are coupled to actuators 22, 24, 26, 28, such as servo actuators that allow a surgeon to manipulate the surgical instruments using a computer mediated control station 20 (FIG. 1). These manipulations may include functions such as positioning, grasping, and moving. Such actuator control of surgical instruments may be referred to as robotic surgery.

A control system couples a computer mediated control station 20 to the robotic actuators 22, 24, 26, 28. As described in more detail in U.S. Pat. No. 6,424,885 entitled "Camera Referenced Control In A Minimally Invasive Surgical Apparatus," the full disclosure of which incorporated herein by reference, the control system will preferably coordinate movement of the input devices with the movement of their associated surgical instruments so that the images of the surgical instruments 402, 404, 406, as displayed to the surgeon, appear at least substantially connected to the input devices in the hands of the surgeon. Further levels of connection will also often be provided to enhance the surgeon's dexterity and ease of use of the surgical instruments 402, 404, 406.

The computer mediated control station 20 may provide hand operated controllers 30 that allow manipulation of the robotic surgical instruments 402, 404, 406 by transmitting signals, such as electrical control signals provided by cables 32, to the actuators 22, 24, 26, 28 that control the actions of the coupled surgical instruments 402, 404, 406. Typically one of the surgical instruments 402 will be a camera instrument that is manipulated to place the remaining surgical instruments and the objects being manipulated within a field of view of the camera. The camera instrument transmits signals to the control station 20 so that an image captured by the camera of the instruments and objects within the field of view can be displayed on a visual display 34 that viewed by the surgeon as the coupled surgical instruments 404, 406 are manipulated. The hand operated controllers 28 and the visual display 30 may be arranged to provide an intuitive control of the surgical instruments 404, 406, wherein the instruments respond in an expected manner to movements of the controllers.

Figures 2, 3:
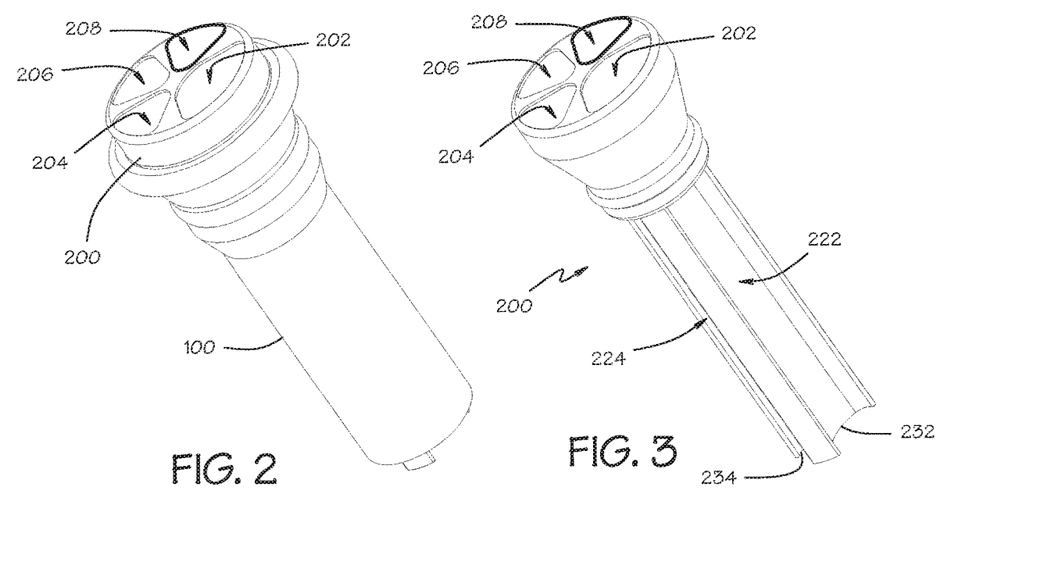
FIG. 2 is a pictorial view of an access port.
FIG. 3 is a pictorial view of an instrument guide.

FIG. 2 shows a pictorial view of an access port that provides the single port access shown in FIG. 1. The access port includes a cannula 100 and an instrument guide 200 that is inserted into the cannula to guide multiple instruments through the cannula to facilitate single port access. It is desirable to minimize the diameter of the cannula 100 so that the incision necessary for placing the cannula in a patient is likewise minimized. The outer wall of the lower portion of the cannula 100 supports and distends the tissues around the incision to provide surgical access while protecting the tissues from injury due to the necessary movements of the surgical instruments.

FIG. 3 is a pictorial view of the instrument guide 200. The instrument guide 200 is configured to fit closely within the cannula 100. The instrument guide 200 includes a number of guide channels 222, 224. Each of the guide channels 222, 224 is configured to support a single surgical instrument 402, 404, 406 at a defined position within the cannula 100. The surgical instruments 402, 404, 406 are inserted into the access port through openings 202, 204, 206, 208 at a proximal end of the instrument guide 200. The surgical instruments 402, 404, 406 are supported by the guide channels 222, 224 until they emerge from a distal end 232, 234 of the instrument guide 200. The instrument guide may be formed from an electrically non-conductive material to aid in electrically isolating the instruments which may carry an electrical charge used for cauterization.

Figures 4, 5:
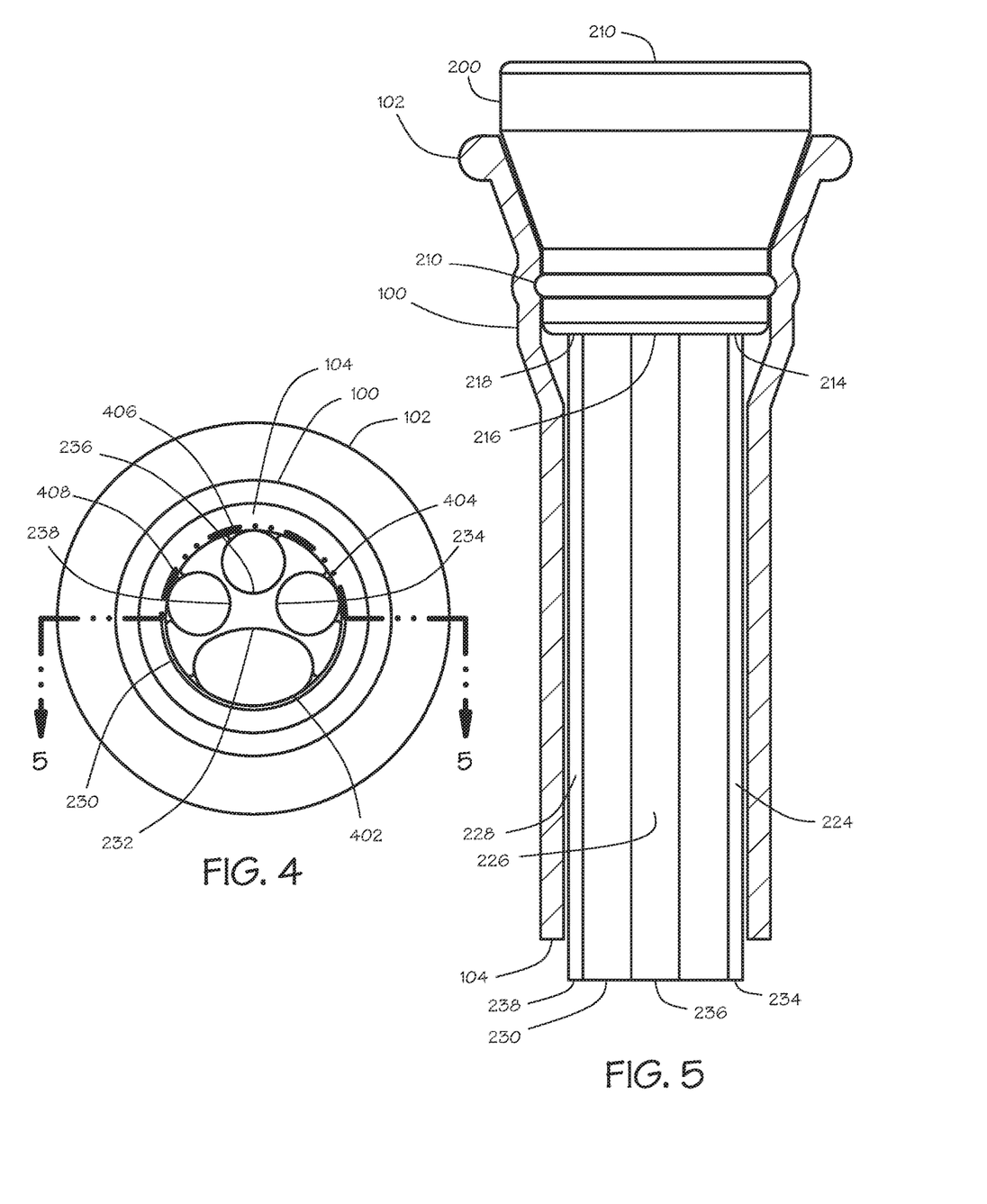
FIG. 4 is a bottom elevation of the access port.
FIG. 5 is a cross-section of the access port along the line 4-4 in FIG. 3.

FIG. 4 is a bottom elevation of the access port. Each of the guide channels is open to the outside surface of the instrument guide. This places a portion of the inserted surgical instruments 402, 404, 406, 408 immediately adjacent the inner wall of the cannula 100 which allows the diameter of the cannula to be minimized. Interstitial portions 230 of the instrument guide 200 support and locate the guide within the cannula 100. The generally cylindrical shape of the instrument guide 200 allows the guide and the inserted surgical instruments to be rotated within the cannula 100.

FIG. 5 is a cross-section of the access port along the line 5-5 in FIG. 4. The proximal end 102 of the cannula 100 has a larger diameter than the distal end 104. The proximal end of the cannula 100 is tapered to a cylindrical lower end having the distal diameter. The cylindrical lower end is the portion of the cannula 100 that is inserted into the incision. The cannula is inserted into the incision and then the instrument guide 200 is inserted into the cannula. The enlarged proximal end 102 and tapered section of the cannula 100 may aid insertion of the instrument guide 200.

The proximal end 210 of the instrument guide 200 is sized and shaped to closely fit the proximal end of the cannula 100. The instrument guide 200 may include a seal 210, such as an O-ring, that couples the instrument guide to the cannula 100 such that the seal retains a pressurized insufflation fluid within the surgical site. The seal 210 may further provide a retention force so that the instrument guide is not lifted from the cannula by the pressure of the insufflation fluid within the surgical site. The guide channels 224, 226, 228 are open to the cannula in the cylindrical lower end and then become closed in the upper proximal end 210. The closed portion of the guide channels 224, 226, 228 may closely fit the surgical instruments 402, 404, 406, 408 to minimize the loss of insufflation fluid past the instruments in the access port. The guide channels 224, 226, 228 may include a seal that minimizes the loss of insufflation fluid when an instrument is not present in the guide channel.

Figures 6, 7:
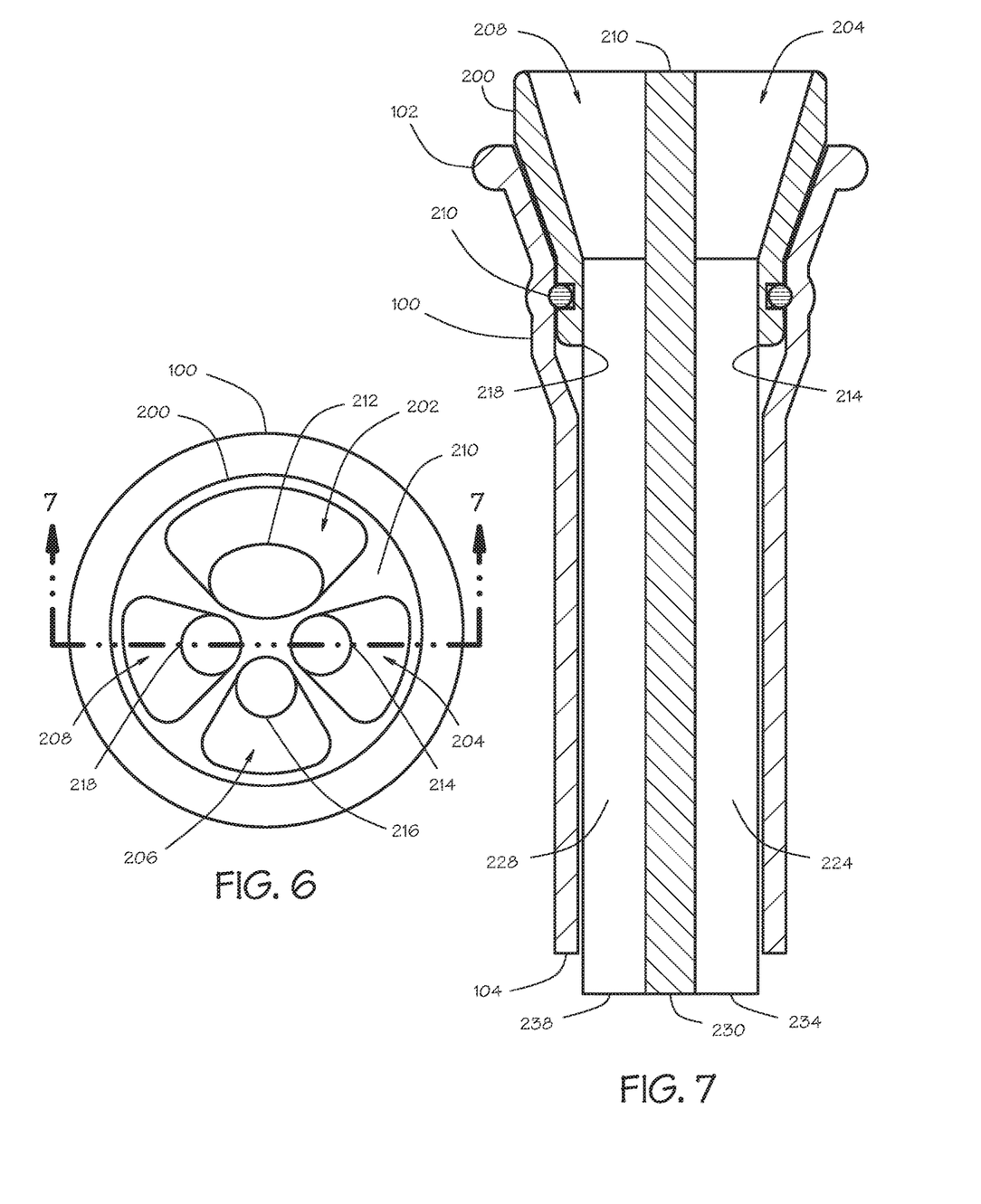
FIG. 6 is a top elevation of the access port.
FIG. 7 is a cross-section of the access port along the line 7-7 in FIG. 6.

FIG. 6 is a top elevation of the access port. The enlarged portions 202, 204, 206, 208 of the guide channels 212, 214, 216, 218 at the proximal (top) end 210 may be seen.

FIG. 7 is a cross-section of the access port along the line 7-7 in FIG. 6. This view shows the guide channels 224, 228 being smoothly enlarged 204, 208 as the channels approaches the proximal end 210 of the instrument guide 200. The enlarged openings and tapered sections may help position instruments within the access port.

Figures 8, 9:
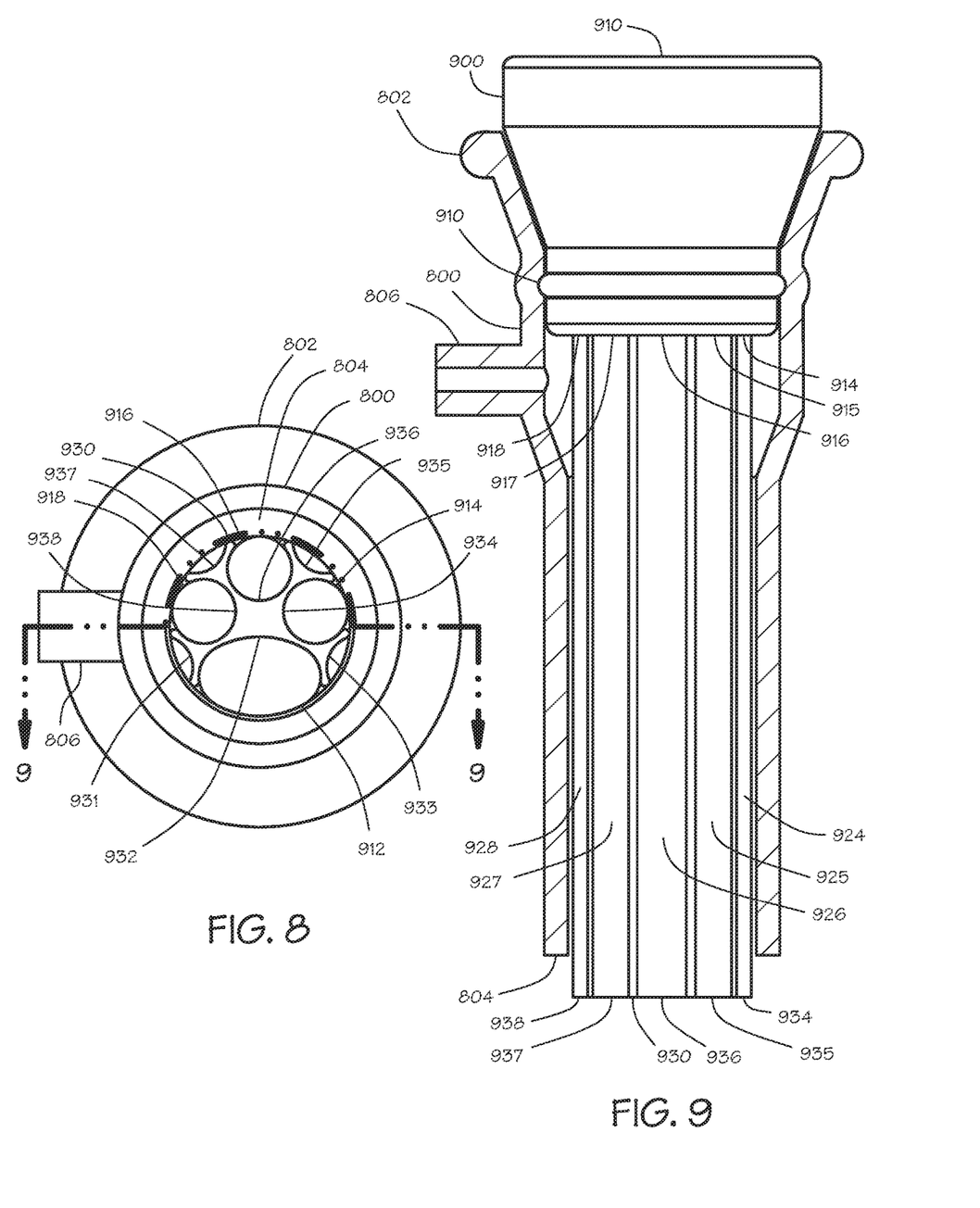
FIG. 8 is a bottom elevation of another access port.
FIG. 9 is a cross-section of the access port along the line 9-9 in FIG. 8.

FIG. 8 is a bottom elevation of yet another access port. FIG. 9 is a cross-section of the access port along the line 9-9 in FIG. 8. In this embodiment, the cannula 800 includes an insufflation port to receive an insufflation fluid. It will be appreciated that the insufflation port is shown in a simplified form and that the insufflation port may include valve and fittings as may be required to connect a source of insufflation fluid and control its flow.

As best seen in the bottom elevation of FIG. 8, the embodiment of the instrument guide 900 shown includes at least one insufflation channel 931, 933, 935, 937. Referring to FIG. 9, each insufflation channel 925, 927 is located between two adjacent guide channels, 924, 926, 928, open at the distal end 935, 937, closed at the proximal end 915, 917, and open along at least a portion of a length of the guide adjacent the proximal end, such that an insufflation fluid introduced into the cannula 800 through the insufflation port 806 flows through the insufflation channel to the surgical site and is retained within the insufflation channel at the proximal end. In another embodiment, the insufflation fluid introduced into the cannula 800 through the insufflation port 806 flows to the surgical site through the clearance between the cannula and the instrument guide without the use of an insufflation channel.

Figures 10, 11, 13, 14:
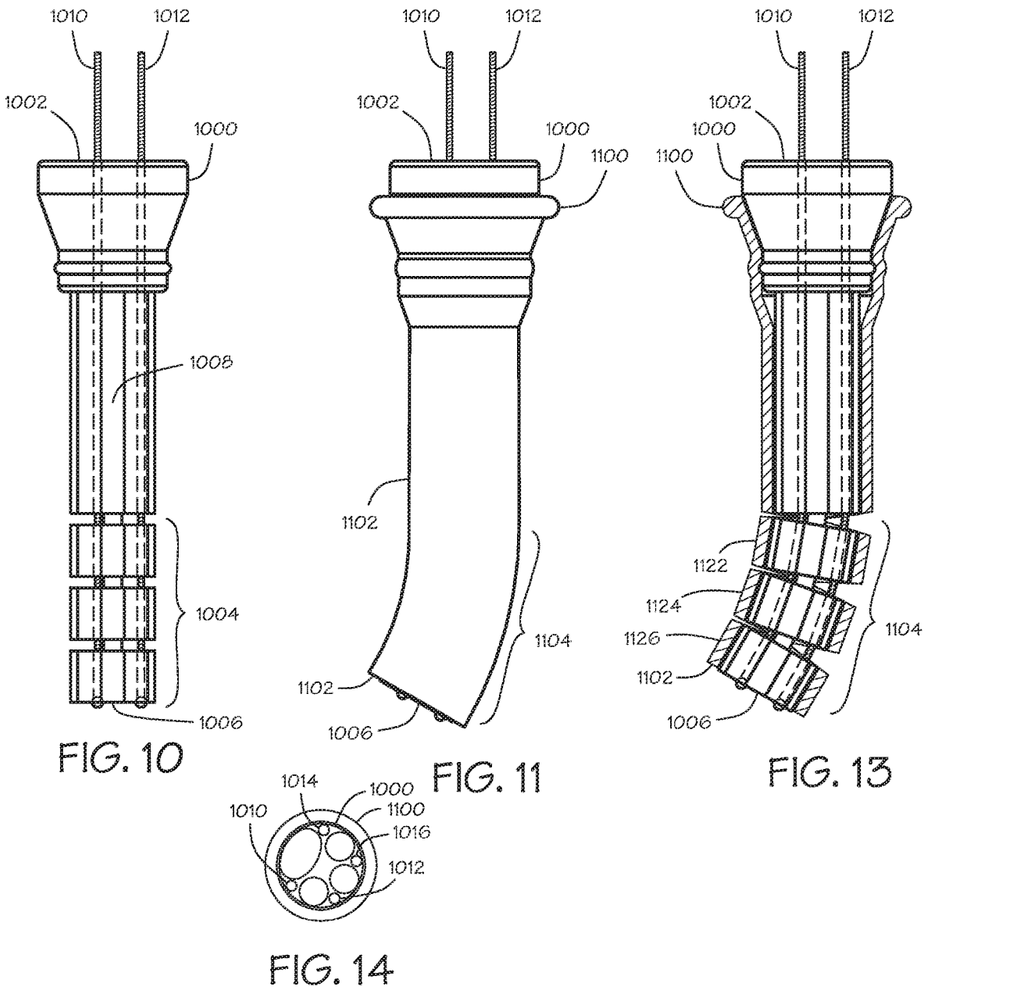
FIG. 10 is a side elevation of another instrument guide.
FIG. 11 is a side elevation of another access port.
FIG. 13 is a cross-section of the access port along the line 13-13 in FIG. 12.
FIG. 14 is an elevation of the bottom end of the access port of FIG. 12.

FIG. 10 is a side view of another instrument guide 1000 for use in minimally invasive surgery that includes a flexible section 1004 at a distal end 1006. This instrument guide 1000 would be used with a flexible surgical instrument having a flexible shaft that conforms to the curve of the instrument guide as the instrument is passed from the proximal end 1002 to the distal end 1006 through the guide channel 1008. In some embodiments, the flexible section 1004 may be adjustable such that the amount and direction of the curvature can be adjusted, such as by pulling on guide cables 1010, 1012.

FIG. 11 is a side view of an access port for use in minimally invasive surgery that includes the instrument guide 1000 with the flexible section and a cannula 1100 with a curved section 1104 extending the cannula lumen 1102. In some embodiments, the curved section 1104 of the cannula 1100 may be a fixed curve to which the flexible section 1004 of the instrument guide 1000 conforms as it is inserted into the cannula. In such embodiments, the guide cables 1010, 1012 may be omitted.

Figure 12:
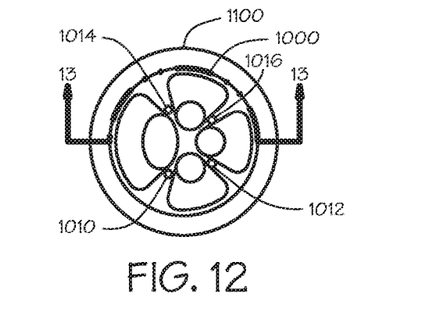
FIG. 12 is a top elevation of the access port of FIG. 11.

FIG. 12 is a top elevation of the access port of FIG. 11. Guide cables 1010, 1012, 1014, 1016 may emerge from the proximal end 1002 to be routed to a backend mechanism. The guide cables may be routed through bores in the instrument guide 1000. The lower end 1104 of the cannula 1100 may be flexible so that the amount and direction of the curvature can be conform to the curvature of the instrument guide 1000. In one embodiment the backend mechanism may lock the flexible section 1004 of the instrument guide 1000 in a desired curvature and orientation. In another embodiment the backend mechanism may include robotic actuators that allow robotic control of the shape and orientation of the flexible section 1004 of the instrument guide 1000. In still other embodiments, the cannula may contain the mechanism for adjusting the amount and direction of the curvature and the instrument guide may conform to the cannula.

FIG. 13 is cross-section view taken along a line corresponding to the line 13-13 in FIG. 12 showing a construction for the flexible section 1104. The flexible section may include jointed links 1122, 1124, 1126. Cables 1010, 1012 may control the curvature of the inserted instrument guide 1000 and thereby steer and/or lock the jointed links of the cannula 1100. It will be appreciated that if jointed links are used to construct an articulated flexible section 1104 in the cannula 1100, a conforming cover (not shown) may be provided to provide a smooth curved surface on the exterior and/or interior of the cannula.

FIG. 14 is a plan view of the distal end 1106 of the cannula 1100 and the distal end 1006 of the inserted instrument guide 1000. If guide cables 1010, 1012, 1014, 1016 are provided, they may pass through bores in the instrument guide 1000 and be coupled to the distal end 1006, such as by balls crimped onto the ends of the guide cables that engage recesses at the distal end of the bores. In other embodiments, the guide cables may pass through the sidewall of the tubular portion 1102 of the cannula 1100.

Figures 15, 16:
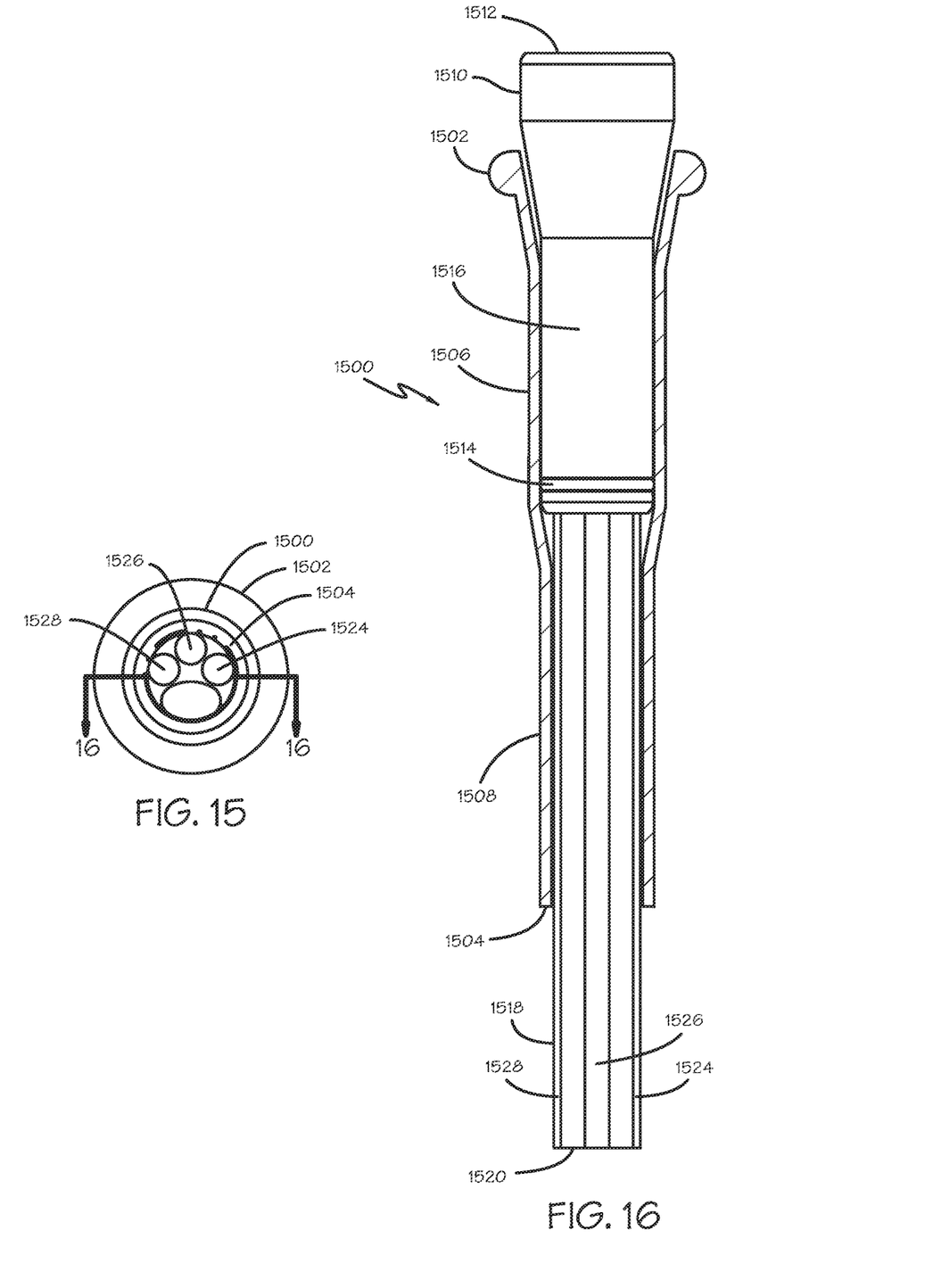
FIG. 15 is a bottom elevation of another access port.
FIG. 16 is a cross-section of the access port along the line 16-16 in FIG. 15.

FIG. 15 is a bottom elevation of another access port. FIG. 16 is a cross-section of the access port along the line 16-16 in FIG. 15. The proximal end 1502 of the cannula 1500 has a larger diameter than the distal end 1504. The proximal end 1502 of the cannula 1500 is tapered to a cylindrical lower end 1508 having the distal diameter. The cylindrical lower end 1508 is the portion of the cannula 1500 that is inserted into the incision. The cannula 1500 is inserted into the incision and then the instrument guide 1510 is inserted into the cannula. The enlarged proximal end 1502 and tapered section of the cannula 1500 may aid insertion of the instrument guide 1510.

The proximal end 1512 of the instrument guide 1510 is sized and shaped to fit the proximal end 1502 of the cannula 1500. In the embodiment shown, the proximal end 1512 of the instrument guide 1510 includes a cylindrical portion 1516 that fits within a corresponding cylindrical portion 1506 of the cannula 1500. The instrument guide 1510 includes a seal 1514, such as an O-ring, that couples the instrument guide to the cylindrical portion 1506 of the cannula 1500 such that the seal retains a pressurized insufflation fluid within the surgical site.

The guide channels 1524, 1526, 1528 of the instrument guide 1510 are open to the cannula 1500 in the cylindrical lower end 1508 of the cannula and then become closed in the upper proximal end 1512. The closed portion of the guide channels 1524, 1526, 1528 may closely fit the surgical instruments to minimize the loss of insufflation fluid past the instruments in the access port. In particular, the guide channels 1524, 1526, 1528 are closed in the cylindrical portion 1516 of the instrument guide 1510 that is above the seal 1514.

The seal 1514 is located on the distal end of the cylindrical portion 1516 so that the instrument guide 1510 seals against the cannula 1500 when the distal end of the cylindrical portion of the instrument guide is at the proximal end of the corresponding cylindrical portion 1506 of the cannula 1500. This permits the instrument guide 1510 to be raised and lowered within the cannula 1500 to facilitate placement of the surgical instruments adjacent the surgical site. In other embodiments, the seal is located at the proximal end of the cylindrical portion 1506 of the cannula 1500.

In the embodiment shown, the lower portion 1518 of the instrument guide 1510 has a length that is sufficient to at least reach the distal end 1504 of the cannula 1500 when the seal 1514 is at the proximal end of the cylindrical portion 1506 of the cannula. Thus the distal end 1520 of the instrument guide 1510 will extend substantially beyond the distal end 1504 of the cannula 1500 when the instrument guide is fully inserted into the cannula. In other embodiments, the instrument guide does not reach the distal end of the cannula in some or all operative positions. The open portion of the guide channels 1524, 1526, 1528 in the lower portion of the instrument guide 1510 surround the surgical instruments sufficiently to provide lateral support of the instruments in the portion of the guide that extends beyond the distal end 1504 of the cannula 1500.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

The invention claimed is:

1. A surgical access port comprising:
   an instrument guide comprising a proximal end, a distal end, a plurality of instrument guide channels between the proximal and distal ends of the instrument guide, and an outside surface that fits closely to an inner wall surface of a cannula into which the instrument guide is inserted; and
   a seal;
   wherein the seal is positioned to seal between the instrument guide and the inner wall surface of the cannula as the instrument guide rotates within the cannula;
   wherein a first guide channel of the plurality of instrument guide channels is configured to support a first surgical instrument at a first defined position within the cannula;
   wherein a second guide channel of the plurality of instrument guide channels is configured to support a second surgical instrument at a second defined position within the cannula; and
   wherein a first guide channel opening is defined along a length of the first guide channel to be open to the outside surface of the instrument guide and place a portion of the first surgical instrument supported by the first guide channel of the instrument guide adjacent the inner wall surface of the cannula.

2. The surgical access port of claim 1:
   wherein a second guide channel opening is defined along a length of the second guide channel to be open to the outside surface of the instrument guide and place a portion of the second surgical instrument supported by the second guide channel of the instrument guide adjacent the inner wall surface of the cannula.

3. The surgical access port of claim 2:
   wherein a cross section of the first guide channel is different from a cross section of a second guide channel.

4. The surgical access port of claim 2:
   wherein an insufflation channel is defined between the first and second instrument guide channel openings.

5. The surgical access port of claim 4:
   wherein the insufflation channel is open to the inner wall surface of the cannula.

6. The surgical access port of claim 2:
   wherein an insufflation channel is defined only from a position between the proximal and distal ends of the instrument guide to the distal end of the instrument guide; and
   wherein the insufflation channel is defined between the first and second guide channel openings.

7. The surgical access port of claim 6:
   wherein the insufflation channel is open to the inner wall surface of the cannula.

8. The surgical access port of claim 1:
   wherein the proximal end of the instrument guide has a larger cross-section than the distal end of the instrument guide.

9. The surgical access port of claim 1:
   wherein the first guide channel is smoothly enlarged at the proximal end of the instrument guide.

10. The surgical access port of claim 1:
    wherein the instrument guide is formed from an electrically non-conductive material.

11. The surgical access port of claim 1:
    wherein a distal end portion of the instrument guide comprises a flexible section.

12. The surgical access port of claim 11:
    wherein the flexible section comprises a plurality of locking cables extending through a corresponding plurality of locking cable channels.

13. The surgical access port of claim 1:
    wherein the distal end of the instrument guide extends beyond a distal end of the cannula.

14. The surgical access port of claim 1:
    wherein each guide channel of the plurality of instrument guide channels extends from the proximal end of the instrument guide to the distal end of the instrument guide.

15. The surgical access port of claim 1:
    wherein the proximal end of the instrument guide fits within a proximal opening of the cannula.

16. A surgical access port comprising:
    means for supporting a first surgical instrument extending through a cannula at a first defined position in the cannula;
    means for supporting a second surgical instrument extending through the cannula at a second defined position in the cannula; and
    means for sealing an insufflation gas;
    wherein the means for supporting the first surgical instrument comprises means for placing a portion of the first surgical instrument adjacent an inner sidewall surface of the cannula;
    wherein the means for supporting the second surgical instrument comprises means for placing a portion of the second surgical instrument adjacent the inner sidewall surface of the cannula;
    wherein the means for supporting the first surgical instrument and the means for supporting the second surgical instrument are comprised in means for rotating the first and second surgical instruments together within the cannula; and
    wherein the means for sealing the insufflation gas is between the means for rotating and the inner sidewall surface of the cannula.

17. The surgical access port of claim 16, further comprising:
    means for directing an insufflation gas between the means for supporting the first surgical instrument and the means for supporting the second surgical instrument.

18. The surgical access port of claim 16, further comprising:
    means for receiving and guiding the first surgical instrument into the means for supporting the first surgical instrument; and
    means for receiving and guiding the second surgical instrument into the means for supporting the second surgical instrument.

19. The surgical access port of claim 16:
    wherein the means for supporting the first surgical instrument comprises means for electrically insulating the first surgical instrument from the second surgical instrument.

20. The surgical access port of claim 16:
wherein the means for supporting the first surgical instrument extends distally within the cannula and past a distal end of the cannula; and
wherein the means for supporting the second surgical instrument extends distally within the cannula and past the distal end of the cannula.

21. The surgical access port of claim 16:
wherein the means for supporting the first surgical instrument fits within a proximal opening of the cannula; and
wherein the means for supporting the second surgical instrument fits within the proximal opening of the cannula.

\* \* \* \* \*